(12) United States Patent
Himmelsbach et al.

(10) Patent No.: US 7,713,938 B2
(45) Date of Patent: May 11, 2010

(54) CRYSTALLINE FORM OF 1-CHLORO-4-(β-D-GLUCOPYRANOS-1-YL)-2-[4-((S)-TETRAHYDROFURAN-3-YLOXY)-BENZYL]-BENZENE, A METHOD FOR ITS PREPARATION AND THE USE THEREOF FOR PREPARING MEDICAMENTS

(75) Inventors: Frank Himmelsbach, Mittelbiberach (DE); Sandra Schmid, Bad Wurzach (DE); Martin Schuehle, Oberhoefen (DE); Hans-Jürgen Martin, Biberach (DE); Matthias Eckhardt, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 361 days.

(21) Appl. No.: 11/406,971

(22) Filed: Apr. 19, 2006

(65) Prior Publication Data

US 2007/0249544 A1 Oct. 25, 2007

(30) Foreign Application Priority Data

May 3, 2005 (EP) ................................. 05009669
Aug. 19, 2005 (EP) ................................. 05018012

(51) Int. Cl.
*A01N 43/04* (2006.01)
*C07H 1/00* (2006.01)
(52) U.S. Cl. ........................... 514/23; 514/25; 536/1.11
(58) Field of Classification Search ........................ None
See application file for complete search history.

(56) References Cited

U.S. PATENT DOCUMENTS

| | | | |
|---|---|---|---|
| 4,602,023 A | 7/1986 | Kiely et al. | |
| 4,786,755 A | 11/1988 | Kiely et al. | |
| 6,414,126 B1 | 7/2002 | Ellesworth et al. | |
| 6,515,117 B2 | 2/2003 | Ellesworth et al. | |
| 6,627,611 B2 | 9/2003 | Tomiyama et al. | |
| 6,774,112 B2 | 8/2004 | Gougoutas | |
| 6,936,590 B2 | 8/2005 | Washburn et al. | |
| 7,169,761 B2 | 1/2007 | Tomiyama et al. | |
| 7,202,350 B2 | 4/2007 | Imamura et al. | |
| 7,371,732 B2 | 5/2008 | Eickelmann et al. | |
| 7,375,090 B2 | 5/2008 | Himmelsbach et al. | |
| 7,393,836 B2 | 7/2008 | Eckhardt et al. | |
| 7,417,032 B2 | 8/2008 | Eckhardt et al. | |
| 7,419,959 B2 | 9/2008 | Eckhardt et al. | |
| 7,579,449 B2 | 8/2009 | Eckhardt et al. | |
| 2002/0137903 A1 | 9/2002 | Ellsworth et al. | |
| 2003/0064935 A1 | 4/2003 | Gougoutas | |
| 2003/0114390 A1 | 6/2003 | Washburn et al. | |
| 2004/0138148 A1 | 7/2004 | Fushimi et al. | |
| 2004/0138439 A1 | 7/2004 | Deshpande et al. | |
| 2005/0065098 A1 | 3/2005 | Fujikura et al. | |
| 2005/0124555 A1 | 6/2005 | Tomiyama et al. | |
| 2005/0209166 A1* | 9/2005 | Eckhardt et al. ............... 514/23 |
| 2006/0009400 A1 | 1/2006 | Eckhardt et al. | |
| 2006/0019948 A1 | 1/2006 | Eckhardt et al. | |
| 2006/0025349 A1 | 2/2006 | Eckhardt et al. | |
| 2006/0035841 A1 | 2/2006 | Eckhardt et al. | |
| 2006/0063722 A1 | 3/2006 | Washburn et al. | |
| 2006/0074031 A1 | 4/2006 | Eckhardt et al. | |
| 2006/0142210 A1 | 6/2006 | Eckhardt et al. | |
| 2006/0189548 A1 | 8/2006 | Himmelsbach et al. | |
| 2006/0234953 A1 | 10/2006 | Himmelsbach et al. | |
| 2006/0251728 A1 | 11/2006 | Himmelsbach et al. | |
| 2006/0258749 A1 | 11/2006 | Eckhardt et al. | |
| 2007/0004648 A1 | 1/2007 | Himmelsbach et al. | |
| 2007/0027092 A1 | 2/2007 | Himmelsbach et al. | |
| 2007/0049537 A1 | 3/2007 | Eckhardt et al. | |
| 2007/0054867 A1 | 3/2007 | Eckhardt et al. | |
| 2007/0073046 A1 | 3/2007 | Eckhardt et al. | |
| 2007/0249544 A1 | 10/2007 | Himmelsbach et al. | |
| 2007/0259821 A1 | 11/2007 | Eckhardt et al. | |
| 2008/0058379 A1 | 3/2008 | Eckhardt et al. | |
| 2009/0023913 A1 | 1/2009 | Eckhardt et al. | |

FOREIGN PATENT DOCUMENTS

| | | |
|---|---|---|
| CA | 2 388 818 A1 | 4/2001 |
| CA | 2 494 177 A1 | 2/2004 |
| CA | 2 508 024 A1 | 6/2004 |
| CA | 2 508 226 A1 | 6/2004 |
| CA | 2539032 A1 | 3/2005 |
| CA | 2 557 269 A1 | 9/2005 |
| CA | 2 557 320 A1 | 9/2005 |

(Continued)

OTHER PUBLICATIONS

Adachi et al., Metabolism, vol. 49, No. 8, 2000, pp. 990-995.*
Tetsuya Adachi et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.
Rachida Benhaddou et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Wolfgang Dohle et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

(Continued)

*Primary Examiner*—Traviss C McIntosh, III
(74) *Attorney, Agent, or Firm*—Michael P. Morris; Edouard G. Lebel; David A. Dow (57) ABSTRACT

The invention relates to a crystalline form of 1-chloro-4-(β-D-glucopyranos-1-yl)-2-[4-((S) -tetrahydrofuran-3-yloxy)-benzyl]-benzene, to a method for the preparation thereof, as well as to the use thereof for preparing medicaments.

7 Claims, 1 Drawing Sheet

FOREIGN PATENT DOCUMENTS

| | | |
|---|---|---|
| CA | 2 557 801 A1 | 10/2005 |
| CA | 2 573 777 A1 | 2/2006 |
| EP | 0 206 567 A2 | 6/1986 |
| EP | 1344780 A1 | 9/2003 |
| EP | 1 385 856 A0 | 2/2004 |
| EP | 1224195 B | 5/2005 |
| EP | 1 553 094 A1 | 7/2005 |
| EP | 1 609 785 A1 | 12/2005 |
| JP | 58/164502 A | 9/1983 |
| JP | 62/030750 A | 2/1987 |
| JP | 11/124392 A | 5/1999 |
| JP | 2001/288178 A | 10/2001 |
| JP | 2003/511458 A | 3/2003 |
| JP | 2004/359630 A | 12/2004 |
| WO | 98/31697 | 7/1998 |
| WO | 01/27128 A1 | 4/2001 |
| WO | 01/74834 A1 | 10/2001 |
| WO | 02/064606 A1 | 8/2002 |
| WO | 02/083066 A2 | 10/2002 |
| WO | 03/099836 A1 | 12/2003 |
| WO | 2004/013118 A1 | 2/2004 |
| WO | 2004/052902 A1 | 6/2004 |
| WO | 2004/052903 A1 | 6/2004 |
| WO | 2004/063209 A2 | 7/2004 |
| WO | 2004/076470 A2 | 9/2004 |
| WO | 2004/080990 A1 | 9/2004 |
| WO | 2005/012326 A1 | 1/2005 |
| WO | 2005/012318 A2 | 2/2005 |
| WO | 2005/085237 A1 | 9/2005 |
| WO | 2005/085265 A1 | 9/2005 |
| WO | 2005/092877 A1 | 10/2005 |
| WO | 2006/011469 A1 | 2/2006 |
| WO | 2006/034489 A2 | 3/2006 |
| WO | 2006/064033 A2 | 6/2006 |
| WO | 2006/089872 A1 | 8/2006 |
| WO | 2006/108842 A1 | 10/2006 |
| WO | 2006/117360 A1 | 11/2006 |
| WO | 2006/120208 A1 | 11/2006 |
| WO | 2007/014894 A2 | 2/2007 |
| WO | 2007/025943 A2 | 3/2007 |
| WO | 2007/028814 A1 | 3/2007 |
| WO | 2007/031548 A2 | 3/2007 |

OTHER PUBLICATIONS

Alois Fuerstner et al; Practical Method for the Rhodium-Catalyzed Addition of Aryl- and Alkenylboronic Acids to Aldehydes; Advanced Synthesis and Catalysis (2001) vol. 343 No. 4 pp. 343-350.

Asanori Hatsuda et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.

Craig A Hutton et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.

Akehiko Iida et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.

G. Erik Jagdmann, Jr; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1645.

Ja Seo Koo et al; 2-Pyridyl Cyanate: A Useful Reagent for he Preparation of Nitriles; Synthetic Communications (1996) vol. 26 No. 20 pp. 3709-3713; Marcel Dekker, Inc.

Takeshi Kuribayashi, et al; c-Glycosylated Aryl tins: Versatile Building Blocks for Aryl C-Glycoside Glycomimetics; J. Carbohydrate Chemistry (1999) vol. 18, No. 4 pp. 371-382.

Takeshi Kuribayashi, et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Takeshi Kuribayashi et al; Bis C-Glycosylated Diphenylmethanes for Stable Glycoepitope Mimetics; Syntletters (1999) vol. 6 pp. 737-740.

Sandrine Langle et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.

Mark McLaughlin et al; Suzuki-Miyaura Cross-Coupling of Benzylic Phospahates with Arylboronic Acids; Organic Letters (2005) vol. 7 No. 22 pp. 4875-4878.

Ouri Neamati, et al, "Depsides and Depsidones as Inhibiton of HIV-1 Integrase: Dimvery of Novel Inhibitors Through 3D Database Searclung", J. Med. Chem., 1997, vol. 40, pp. 942-951.

Sabrina M. Nobre et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.

Akira Oku, et al; T-1095, An Inhibitor or renal $Na^+$-Glucose Cotransporters, May Provide a Novel Approach to Treating Diabetes; Diabetes (1999) vol. 48 pp. 1794-1800.

Richard J. Perner et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.

Michael Bech Sommer et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.

Lasslo Revesz et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.

Federica Stazi et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.

Rik R. Tykwinski; Evolution in the Palladium-Catalyzed Cross-Coupling of sp- and sp2-Hybridized Carbon Atoms; Angew Chemical International Edition (2003) vol. 42 pp. 1566-1568.

Kiichiro Ueta, et al; Long-Term Treatment with the $Na^+$-Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.

Debra J. Wallace et al; Cyclopropylboronic Acid: Synthesis and Suzuki Cross-Coupling Reactions; Tetrahedron Letters (2002) vol. 43 pp. 6987-6990; Pergamon Press.

Song Xue et al; Zinc-mediated Synthesis of Alpha-C-Glycosided from 1,2-Anhydroglycosides; Synletters (2003) vol. 6 pp. 870-872.

International Search Report for PCT/EP2005/002618 mailed Jun. 30, 2005.

International Search Report for PCT/EP2006/061956 mailed Jul. 5, 2006.

International Search Report for PCT/EP2006/061957 mailed Jul. 5, 2006.

International Search Report for PCT/EP2006/061520 mailed Jul. 26, 2006.

International Search Report for PCT/EP2006/062191 mailed Aug. 8, 2006.

International Search Report for PCT/EP2005/056806 mailed Dec. 27, 2006.

International Search Report for PCT/EP2006/066107 mailed Jan. 11, 2007.

International Search Report for PCT/EP2006/066347 mailed Mar. 7, 2007.

International Search Report for PCT/EP2006/065710 mailed Mar. 8, 2007.

International Search Report for PCT/EP2007/051411 mailed May 2, 2007.

International Search Report for PCT/EP2007/054248 mailed Jun. 18, 2007.

International Search Report for PCT/EP2006/064702 mailed Jul. 26, 2007.

Non-Final Office Action dated Jun. 24, 2008 from U.S. Appl. No. 11/406,971, filed Apr. 19, 2006.

Non-Final Office Action dated Jun. 5, 2008 from U.S. Appl. No. 11/408,899, filed Apr. 21, 2006.
Non Final Office Action dated Apr. 2, 2008 from U.S. Appl. No. 11/674,839, filed Feb. 14, 2007.
Response to Non-Final Office Action dated Apr. 2, 2008 from U.S. Appl. No. 11/674,839, filed Feb. 14, 2007.
Non Final Office Action dated Apr. 2, 2008 from U.S. Appl. No. 11/742,612, filed May 1, 2007.
Response to Non-Final Office Action dated Apr. 2, 2008 from U.S. Appl. No. 11/742,612, filed May 1, 2007.
U.S. Appl. No. 12/545,175 filed Aug. 21, 2009.
Non-Final Office Action dated May 8, 2008 from U.S. Appl. No. 11/359,846 filed Feb. 22, 2006.

Notice of Allowance and Fee(s) Due dated Jan. 13, 2009 from U.S. Appl No. 11/304,284 filed Dec. 15, 2005.
Notice of Allowance and Fee(s) Due dated Dec. 30, 2008 from U.S. Appl. No. 11/674,839 filed Feb. 14, 2007.
Notice of Allowance and Fee(s) Due dated Feb. 3, 2009 from U.S. Appl. No. 11/359,846 filed Feb. 22, 2006.
Notice of Allowance and Fee(s) Due dated Jan. 2, 2009 from U.S. Appl. No. 11/742,612 filed May 1, 2007.
Response dated Nov. 5, 2008 to Non-Final Office Action dated May 8, 2008 from U.S. Appl. No. 11/359,846 filed Feb. 22, 2006.

* cited by examiner

Figure 1: X-ray powder diffraction pattern of the crystalline form

Figure 2: DSC and TG diagram of the crystalline form

CRYSTALLINE FORM OF 1-CHLORO-4-(β-D-GLUCOPYRANOS-1-YL)-2-[4-((S)-TETRAHYDROFURAN-3-YLOXY)-BENZYL]-BENZENE, A METHOD FOR ITS PREPARATION AND THE USE THEREOF FOR PREPARING MEDICAMENTS

RELATED APPLICATIONS

This application claims benefit to EP 05009699, filed May 3, 2005 and EP 05018012 filed Aug. 19, 2005 the contents of which are incorporated herein.

THE INVENTION

The invention relates to a crystalline form of 1-chloro-4-(β-D-glucopyranos-1-yl)-2-[4-((S)-tetrahydrofuran-3-yloxy)-benzyl]-benzene, to a method for the preparation thereof, as well as to the use thereof for preparing medicaments.

BACKGROUND OF THE INVENTION

The compound 1-chloro-4-(β-D-glucopyranos-1-yl)-2-[4-((S)-tetrahydrofuran-3-yloxy)-benzyl]-benzene (in the following referred to it as "compound A") is described in the international patent application WO 2005/092877 and has the chemical structure according to formula A The compounds described therein have a valuable inhibitory effect on the sodium-dependent glucose cotransporter SGLT, particularly SGLT2. The method of manufacture of the compound A as described therein does not yield a crystalline form.

A certain phamaceutical activity is of course the basic prerequisite to be fulfilled by a pharmaceutically active agent before same is approved as a medicament on the market. However, there are a variety of additional requirements a pharmaceutically active agent has to comply with. These requirements are based on various parameters which are connected with the nature of the active substance itself. Without being restrictive, examples of these parameters are the stability of the active agent under various environmental conditions, its stability during production of the pharmaceutical formulation and the stability of the active agent in the final medicament compositions. The pharmaceutically active substance used for preparing the pharmaceutical compositions should be as pure as possible and its stability in long-term storage must be guaranteed under various environmental conditions. This is essential to prevent the use of pharmaceutical compositions which contain, in addition to the actual active substance, breakdown products thereof, for example. In such cases the content of active substance in the medicament might be less than that specified.

Uniform distribution of the medicament in the formulation is a critical factor, particularly when the medicament has to be given in low doses. To ensure uniform distribution, the particle size of the active substance can be reduced to a suitable level, e.g. by grinding. Since breakdown of the pharmaceutically active substance as a side effect of the grinding (or micronising) has to be avoided as far as possible, in spite of the hard conditions required during the process, it is essential that the active substance should be highly stable throughout the grinding process. Only if the active substance is sufficiently stable during the grinding process it is possible to produce a homogeneous pharmaceutical formulation which always contains the specified amount of active substance in a reproducible manner.

Another problem which may arise in the grinding process for preparing the desired pharmaceutical formulation is the input of energy caused by this process and the stress on the surface of the crystals. This may in certain circumstances lead to polymorphous changes, to amorphization or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

The stability of a pharmaceutically active substance is also important in pharmaceutical compositions for determining the shelf life of the particular medicament; the shelf life is the length of time during which the medicament can be administered without any risk. High stability of a medicament in the abovementioned pharmaceutical compositions under various storage conditions is therefore an additional advantage for both the patient and the manufacturer.

The absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. Preferably, therefore, a pharmaceutically active substance should be only slightly hygroscopic.

Furthermore, the availability of a well-defined crystalline form allows the purification of the drug substance by recrystallization.

Apart from the requirements indicated above, it should be generally borne in mind that any change to the solid state of a pharmaceutical composition which is capable of improving its physical and chemical stability gives a significant advantage over less stable forms of the same medicament.

The aim of the invention is thus to provide a stable crystalline form of the compound A which meets important requirements imposed on pharmaceutically active substances as mentioned above.

OBJECT OF THE INVENTION

In a first aspect the present invention relates to a crystalline form of the compound A.

In a second aspect the present invention relates to the crystalline form of the compound A having an X-ray powder diffraction pattern that comprises peaks at 18.84, 20.36 and 25.21 degrees $2\Theta$ ($\pm 0.05$ degrees $2\Theta$, wherein said X-ray powder diffraction pattern is made using $CuK_{\alpha 1}$ radiation.

In a third aspect the present invention relates to the compound A wherein at least 50% of said substance is present in the form of a crystalline form as defined hereinbefore and hereinafter.

In the light of the pharmaceutical efficacy of the compound A a fourth aspect of the present invention relates to a pharmaceutical composition or medicament comprising a crystalline form as defined hereinbefore and hereinafter.

In a fifth aspect the present invention relates to a use of a crystalline form as defined hereinbefore or hereinafter for preparing a pharmaceutical composition which is suitable for the treatment or prevention of diseases or conditions which can be influenced by inhibiting sodium-dependent glucose cotransporter SGLT, preferably SGLT2.

In a sixth aspect the present invention relates to a use of a crystalline form as defined hereinbefore or hereinafter for preparing a pharmaceutical composition which is suitable for the treatment or prevention of metabolic disorders.

In a seventh aspect the present invention relates to a use of a crystalline form as defined hereinbefore or hereinafter for preparing a pharmaceutical composition for inhibiting the sodium-dependent glucose cotransporter SGLT2.

In a eighth aspect the present invention relates to a use of a crystalline form as defined hereinbefore or hereinafter for preparing a pharmaceutical composition for preventing the degeneration of pancreatic beta cells and/or for improving and/or restoring the functionality of pancreatic beta cells.

In an ninth aspect the present invention relates to a use of a crystalline form as defined hereinbefore and hereinafter for preparing a pharmaceutical composition for preventing, slowing, delaying or treating diseases or conditions attributed to an abnormal accumulation of liver fat in a patient in need thereof.

In an tenth aspect the present invention relates to a method for making the crystalline form as defined hereinbefore and hereinafter, said method comprising the following steps:
(a) dissolving compound A in a solvent or a mixture of solvents to form a saturated or nearly saturated solution;
(b) storing preferably with cooling the solution to precipitate the crystalline form and thus to yield a suspension;
(c) isolating the precipitate from the suspension; and
(d) drying the precipitate until any excess of said solvent or mixture of solvents has been removed.

Further aspects of the present invention become apparent to the one skilled in the art from the following detailed description of the invention and the examples.

BRIEF DESCRIPTION OF THE FIGURES

The FIG. 1 shows an X-ray powder diffractogram of the crystalline form.

The FIG. 2 shows the thermoanalysis and determination of the melting point via DSC of the crystalline form.

DETAILED DESCRIPTION OF THE INVENTION

Surprisingly, it has been found that there exists a crystalline form of the compound A which fulfills important requirements mentioned hereinbefore. Accordingly the present invention relates to a crystalline form of the compound A.

This crystalline form may be identified by means of their characteristic X-ray powder diffraction (XRPD) patterns.

The crystalline form is characterised by an X-ray powder diffraction pattern that comprises peaks at 18.84, 20.36 and 25.21 degrees 2$\Theta$ (±0.05 degrees 2$\Theta$, wherein said X-ray powder diffraction pattern is made using CuK$\alpha_1$ radiation.

In particular said X-ray powder diffraction pattern comprises peaks at 14.69, 18.84, 19.16, 19.50, 20.36 and 25.21 degrees 2$\Theta$ (±0.05 degrees 2$\Theta$, wherein said X-ray powder diffraction pattern is made using CuK$\alpha_1$ radiation.

More specifically, the crystalline form is characterised by an X-ray powder diffraction pattern, made using CuK$\alpha_1$ radiation, which comprises peaks at degrees 2$\Theta$ (±0.05 degrees 2$\Theta$ as contained in Table 1.

TABLE 1

| X-ray powder diffraction pattern of the crystalline form (only peaks up to 30° in 2 $\Theta$ are listed): | | |
|---|---|---|
| 2 $\Theta$ [°] | d-value [Å] | Intensity I/I$_0$ [%] |
| 4.46 | 19.80 | 8 |
| 9.83 | 8.99 | 4 |
| 11.68 | 7.57 | 4 |
| 13.35 | 6.63 | 14 |
| 14.69 | 6.03 | 42 |
| 15.73 | 5.63 | 16 |
| 16.20 | 5.47 | 8 |
| 17.95 | 4.94 | 30 |
| 18.31 | 4.84 | 22 |
| 18.43 | 4.81 | 23 |
| 18.84 | 4.71 | 100 |
| 19.16 | 4.63 | 42 |
| 19.50 | 4.55 | 31 |
| 20.36 | 4.36 | 74 |
| 20.55 | 4.32 | 13 |
| 21.18 | 4.19 | 11 |
| 21.46 | 4.14 | 13 |
| 22.09 | 4.02 | 19 |
| 22.22 | 4.00 | 4 |
| 22.71 | 3.91 | 28 |
| 23.44 | 3.79 | 27 |
| 23.72 | 3.75 | 3 |
| 24.09 | 3.69 | 3 |
| 24.33 | 3.66 | 7 |
| 24.81 | 3.59 | 24 |
| 25.21 | 3.53 | 46 |
| 25.65 | 3.47 | 23 |
| 26.40 | 3.37 | 2 |
| 26.85 | 3.32 | 8 |
| 27.26 | 3.27 | 17 |
| 27.89 | 3.20 | 2 |
| 28.24 | 3.16 | 3 |
| 29.01 | 3.08 | 4 |
| 29.41 | 3.03 | 18 |

Figure 1:
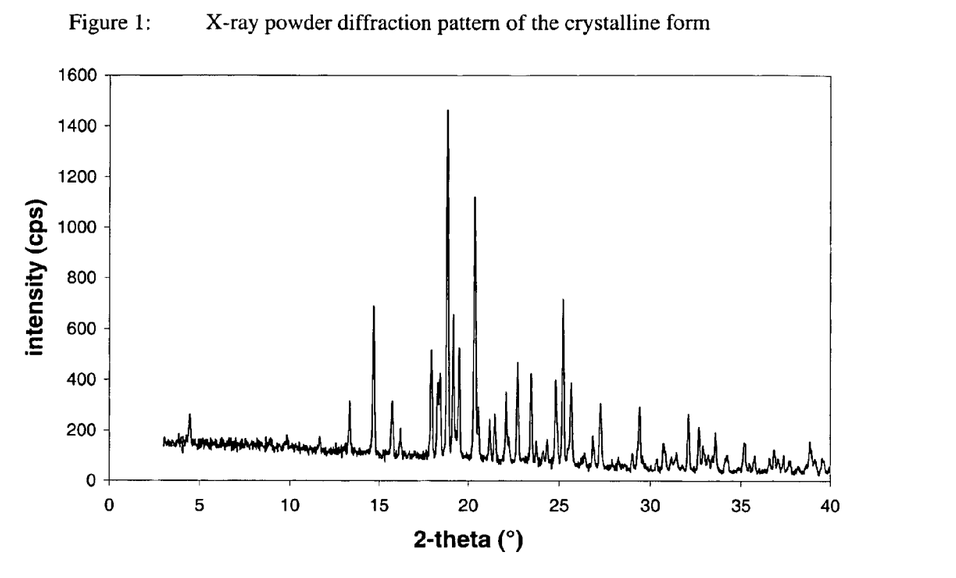

Even more specifically, the crystalline form is characterised by an X-ray powder diffraction pattern, made using CuK$\alpha_1$ radiation, which comprises peaks at degrees 2$\Theta$ (±0.05 degrees 2$\Theta$ as shown in FIG. 1.

Figure 2:
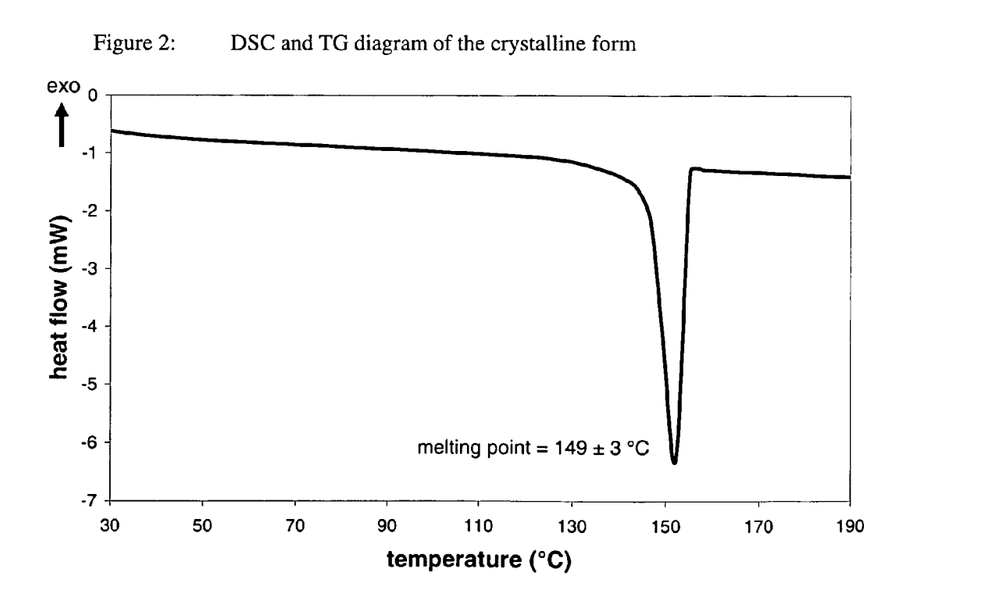

Furthermore the crystalline form of compound A is characterised by a melting point of about 149° C. ±3° C. (determined via DSC; evaluated as onset-temperature; heating rate 10 K/min). The obtained DSC curve is shown in FIG. 2.

The X-ray powder diffraction patterns are recorded, within the scope of the present invention, using a STOE-STADI P—diffractometer in transmission mode fitted with a location-sensitive detector (OED) and a Cu-anode as X-ray source (CuK$\alpha$1 radiation, $\alpha$=1,54056 Å, 40kV, 40 mA). In the Table 1 above the values "2$\Theta$ [°]" denote the angle of diffraction in degrees and the values "d [Å]" denote the specified distances in Å between the lattice planes. The intensity shown in the FIG. 1 is given in units of cps (counts per second).

In order to allow for experimental error, the above described 2 $\Theta$ values should be considered accurate to ±0.05 degrees 2 $\Theta$. That is to say, when assessing whether a given sample of crystals of the compound A is the crystalline form in accordance with the invention, a 2 $\Theta$ value which is experimentally observed for the sample should be considered identical with a characteristic value described above if it falls within ±0.05 degrees 2 $\Theta$ of the characteristic value.

The melting point is determined by DSC (Differential Scanning Calorimetry) using a DSC 821 (Mettler Toledo).

A further aspect of the present invention relates to a method for making the crystalline form of the compound A as defined hereinbefore and hereinafter, said method comprising the following steps:

(a) dissolving compound A in a solvent or a mixture of solvents to form a saturated or nearly saturated solution;
(b) storing the solution to precipitate the crystalline form out of solution;
(c) removing the precipitate from the solution; and
(d) drying the precipitate until any excess of said solvent or mixture of solvents has been removed.

The terms "saturated" or "nearly saturated" are related to the starting material of the compound A as used in step (a). For example a solution which is saturated with respect to the starting material of the compound A may be supersaturated with respect to its crystalline form.

Suitable solvents are preferably selected from the group consisting of $C_{1-4}$-alkanols, water, ethylacetate, acetonitrile, acetone, diethylether and mixture of two or more of these solvents.

More preferred solvents are selected from the group consisting of methanol, ethanol, isopropanol, ethyl acetate, diethylether, acetone, water and mixture of two or more of these solvents, in particular mixtures of one or more of said organic solvents with water.

Particularly preferred solvents are selected from the group consisting of ethylacetate, ethanol, isopropanol and mixtures of ethanol and/or isopropanol with water.

In case a mixture of water and one or more $C_{1-4}$-alkanols, in particular of methanol, ethanol and/or isopropanol, most preferably of ethanol, is taken, a preferred volume ratio of water: the alkanol is in the range from about 1:4 to 4:1; more preferably from about 1:2 to 2:1; even more preferably from about 2:3 to 3:2.

Preferably the step (a) is carried at about room temperature (about 20° C.) or at an elevated temperature up to about the boiling point of the solvent or mixture of solvents used.

In order to reduce the solubility of the compound A in the solution, in step (a) and/or in step (b) one or more antisolvents or non-solvents may be added, preferably during step (a) or at the beginning of step (b). Water is an example of a suitable antisolvent or non-solvent. The amount of antisolvent or non-solvent or of a mixture thereof is preferably chosen to obtain a supersaturated or nearly supersaturated solution.

In step (b) the solution is stored for a time sufficient to obtain a precipitate. The temperature of the solution in step (b) is about the same as or lower than in step (a). During the storing the temperature of the solution containing the compound A is preferably lowered, preferably to a temperature in the range of 20° C. to 0° C. or even lower. The step (b) can be carried out with or without stirring. As known to the one skilled in the art by the period of time and the difference of temperature in step (b) the size, shape and quality of the obtained crystals can be varied. Furthermore the crystallization may be induced by methods as known in the art, for example by scratching or rubbing. Optionally the (nearly) saturated solution may be inoculated with seed crystals.

In step (c) the solvent(s) can be removed from the precipitate by known methods as for example filtration, suction filtration, decantation or centrifugation.

In step (d) an excess of the solvent(s) is removed from the precipitate by methods known to the one skilled in the art as for example by reducing the partial pressure of the solvent(s), preferably in vacuum, and/or by heating above ca. 20° C., preferably in a temperature range below 80° C., even more preferably below 50° C.

The compound A may be synthesized by methods as specifically and/or generally described or cited in the international application WO 2005/092877. Furthermore the biological properties of the compound A may be investigated as it is described in the international application WO 2005/092877 which in its enterity is incorporated herein by reference.

The crystalline form in accordance with the invention is preferably employed as drug active substance in substantially pure form, that is to say, essentially free of other crystalline forms of the compound A. Nevertheless, the invention also embraces the crystalline form as herein defined in admixture with another crystalline form or forms. Should the drug active substance be a mixture of crystalline forms, it is preferred that the substance comprises at least 50% of the crystalline form as described herein.

In view of their ability to inhibit the SGLT activity, the crystalline form according to the invention is suitable for the preparation of pharmaceutical compositions for the treatment and/or preventative treatment of all those conditions or diseases which may be affected by the inhibition of the SGLT activity, particularly the SGLT-2 activity. Therefore, the crystalline form is particularly suitable for the preparation of pharmaceutical compositions for prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. The crystalline form is also suitable for the preparation of pharmaceutical compositions for preventing beta-cell degeneration such as e.g. apoptosis or necrosis of pancreatic beta cells. The crystalline form is also suitable for the preparation of pharmaceutical compositions for improving or restoring the functionality of pancreatic cells, and also of increasing the number and size of pancreatic beta cells. The crystalline form according to the invention may also be used for the preparation of pharmaceutical compositions usefull as diuretics or antihypertensives and suitable for the prevention and treatment of acute renal failure.

By the administration of the crystalline form according to this invention an abnormal accumulation of fat in the liver may be reduced or inhibited. Therefore according to another aspect of the present invention there is provided a method for preventing, slowing, delaying or treating diseases or conditions attributed to an abnormal accumulation of liver fat in a patient in need thereof characterized in that a pharmaceutical composition according to the present invention is administered. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver or toxic fatty liver.

In particular, the crystalline form according to the invention is suitable for the preparation of pharmaceutical compositions for the prevention or treatment of diabetes, particularly type 1 and type 2 diabetes mellitus, and/or diabetic complications.

In addition the crystalline form according to the invention is particularly suitable for the prevention or treatment of overweight, obesity (including class I, class II and/or class III obesity), visceral obesity and/or abdominal obesity.

The dosage required to achieve the corresponding activity for treatment or prevention usually depends on the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the pharmaceutical compositions according to this invention preferably comprise the crystalline form together with one or more inert conventional carriers and/or diluents. Such pharmaceutical compositions may be formulated as conventional galenic preparations such as plain or coated tablets, capsules, powders, suspensions or suppositories.

The following example of synthesis serves to illustrate a method of preparing the compound A and its crystalline form. It is to be regarded only as a possible method described by way of example, without restricting the invention to its contents.

Preparation of the Starting Compounds:

EXAMPLE I

(5-bromo-2-chloro-phenyl)-(4-methoxy-phenyl)-methanone 38.3 ml oxalyl chloride and 0.8 ml of dimethylformamide are added to a mixture of 100 g of 5-bromo-2-chloro-benzoic acid in 500 ml dichloromethane. The reaction mixture is stirred for 14 h, then filtered and separated from all volatile constituents in the rotary evaporator. The residue is dissolved in 150 ml dichloromethane, the solution is cooled to −5° C., and 46.5 g of anisole are added. Then 51.5 g of aluminum trichloride are added batchwise so that the temperature does not exceed 5° C. The solution is stirred for another 1 h at 1 to 5° C. and then poured onto crushed ice. The organic phase is separated, and the aqueous phase is extracted another three times with dichloromethane. The combined organic phases are washed with aqueous 1 M hydrochloric acid, twice with aqueous 1 M sodium hydroxide solution and with brine. Then the organic phase is dried, the solvent is removed and the residue is recrystallised in ethanol.

Yield: 86.3 g (64% of theory)

Mass spectrum (ESI$^+$): m/z=325/327/329 (Br+Cl) [M+H]$^+$

EXAMPLE II

4-bromo-1-chloro-2-(4-methoxy-benzyl)-benzene

A solution of 86.2 g (5-bromo-2-chloro-phenyl)-(4-methoxy-phenyl)-methanone and 101.5 ml triethylsilane in 75 ml dichloromethane and 150 ml acetonitrile is cooled to 10° C. Then with stirring 50.8 ml of boron trifluoride etherate are added so that the temperature does not exceed 20° C. The solution is stirred for 14 h at ambient temperature, before another 9 ml triethylsilane and 4.4 ml boron trifluoride etherate are added. The solution is stirred for a further 3 h at 45 to 50° C. and then cooled to ambient temperature. A solution of 28 g potassium hydroxide in 70 ml of water is added, and the resulting mixture is stirred for 2 h. Then the organic phase is separated off and the aqueous phase is extracted another three times with diisopropylether. The combined organic phases are washed twice with aqueous 2 M potassium hydroxide solution and once with brine and then dried over sodium sulfate. After the solvent has been removed the residue is washed in ethanol, separated again and dried at 60° C.

Yield: 50.0 g (61% of theory)

Mass spectrum (ESI$^+$): m/z=310/312/314 (Br+Cl) [M+H]$^+$

EXAMPLE III

4-(5-bromo-2-chloro-benzyl)-phenol

A solution of 14.8 g 4-bromo-1-chloro-2-(4-methoxy-benzyl)-benzene in 150 ml dichloromethane is cooled in an ice bath. Then 50 ml of a 1 M solution of boron tribromide in dichloromethane are added, and the solution is stirred for 2 h at ambient temperature. The solution is then cooled in an ice bath again, and saturated aqueous potassium carbonate solution is added dropwise. At ambient temperature the mixture is adjusted with aqueous 1 M hydrochloric acid to a pH of 1, the organic phase is separated, and the aqueous phase is extracted another three times with ethyl acetate. The combined organic phases are dried over sodium sulphate, and the solvent is removed completely.

Yield: 13.9 g (98% of theory)

Mass spectrum (ESI$^-$): m/z=295/297/299 (Br+Cl) [M−H]$^-$

EXAMPLE IV

[4-(5-bromo-2-chloro-benzyl)-phenoxy]-tert-butyl-dimethyl-silane

A solution of 13.9 g 4-(5-bromo-2-chloro-benzyl)-phenol in 140 ml dichloromethane is cooled in an ice bath. Then 7.54 g tert-butyldimethylsilylchlorid in 20 ml dichloromethane are added followed by 9.8 ml triethylamine and 0.5 g 4-dimethylaminopyridine. The solution is stirred for 16 h at ambient temperature and then diluted with 100 ml dichloromethane. The organic phase is washed twice with aqueous 1 M hydrochloric acid and once with aqueous sodium hydrogen carbonate solution and then dried over sodium sulfate. After the solvent has been removed the residue is filtered through silica gel (cyclohexane/ethyl acetate 100:1).

Yield: 16.8 g (87% of theory)

Mass spectrum (EI): m/z=410/412/414 (Br+Cl) [M]$^+$

EXAMPLE V

2,3,4,6-tetrakis-O-(trimethylsilyil-D-glucopyranone

A solution of 20 g D-glucono-1,5-lactone and 98.5 ml N-methylmorpholine in 200 ml of tetrahydrofuran is cooled to −5° C. Then 85 ml trimethylsilylchloride are added dropwise so that the temperature does not exceed 5° C. The solution is then stirred for 1 h at ambient temperature, 5 h at 35° C. and again for 14 h at ambient temperature. After the addition of 300 ml of toluene the solution is cooled in an ice bath, and 500 ml of water are added so that the temperature does not exceed 10° C. The organic phase is then separated and washed in each case once with aqueous sodium dihydrogen phosphate solution, water and brine. The solvent is removed, the residue is taken up in 250 ml of toluene, and the solvent is again removed completely.

Yield: 52.5 g (approx. 90% pure)

Mass spectrum (ESI$^+$): m/z=467 [M+H]$^+$

EXAMPLE VI 1-chloro-4-(β-D-glucopyranos-1-yl)-2-(4-hydroxy-benzyl)-benzene

A solution of 4.0 g [4-(5-bromo-2-chloro-benzyl)-phenoxy]-tert-butyl-dimethyl-silane in 42 ml dry diethyl ether is cooled to −80° C. under argon. 11.6 ml of a 1.7 M solution of tert-butyllithium in pentane are slowly added dropwise to the cooled solution, and then the solution is stirred for 30 min at −80° C. This solution is then added dropwise through a transfer needle, which is cooled with dry ice, to a solution of 4.78 g 2,3,4,6-tetrakis-O-(trimethylsilyl)-D-glucopyranone in 38 ml diethyl ether chilled to −80° C.

The resulting solution is stirred for 3 h at −78° C. Then a solution of 1.1 ml methanesulphonic acid in 35 ml of methanol is added and the solution is stirred for 16 h at ambient temperature. The solution is then neutralised with solid sodium hydrogen carbonate, ethyl acetate is added and the methanol is removed together with the ether. Aqueous sodium hydrogen carbonate solution is added to the remaining solution, and the resulting mixture is extracted four times with ethyl acetate. The organic phases are dried over sodium sulphate and evaporated down. The residue is dissolved in 30 ml acetonitrile and 30 ml dichloromethane and the solution is cooled to −10° C. After the addition of 4.4 ml triethylsilane 2.6 ml boron trifluoride etherate are added dropwise so that the temperature does not exceed −5° C. After the addition is complete the solution is stirred for another 5 h at −5 to −10° C. and then quenched by the addition of aqueous sodium hydrogen carbonate solution. The organic phase is separated, and the aqueous phase is extracted four times with ethyl acetate. The combined organic phases are dried over sodium sulfate, the solvent is removed, and the residue is purified by chromatography on silica gel (dichoromethane/methanol 1:0->3:1). The product then obtained is an approx. 6:1 mixture of β/α which can be converted into the pure β-anomer by global acetylation of the hydroxy groups with acetic anhydride and pyridine in dichloromethane and recrystallization of the product from ethanol. The product thus obtained is converted into the title compound by deacetylation in methanol with aqueous 4 M potassium hydroxide solution.

Yield: 1.6 g (46% of theory)

Mass spectrum (ESI$^+$): m/z=398/400 (Cl) [M+H]$^+$

Preparation of the Compound A:

1-chloro-4-(β-D-glucopyranos-1-yl)-2-[4-((S)-tetrahydrofuran-3-yloxy)-benzyl]-benzene 0.19 g (R)-3-(4-methylphenylsulfonyloxy)-tetrahydrofuran are added to a mixture of 0.20 g 1-chloro-4-(β-D-glucopyranos-1-yl)-2-(4-hydroxybenzyl)-benzene and 0.29 g cesium carbonate in 2.5 ml dimethylformamide. The mixture is stirred at 75° C. for 4 h, before another 0.29 g caesium carbonate and 0.19 g (R)-3-(4-methylphenyl-sulfonyloxy)-tetrahydrofuran are added. After an additional 14 h stirring at 75° C. the mixture is cooled to ambient temperature and brine is added. The resulting mixture is extracted with ethyl acetate, the combined organic extracts are dried over sodium sulfate, and the solvent is removed. The residue is purified by chromatography on silica gel (dichloromethane/methanol 1:0->5:1).

Yield: 0.12 g (49% of theory)

Mass spectrum (ESI$^+$): m/z=451/453 (Cl) [M+H]$^+$

Preparation of the Crystalline Form:

Variant 1:

30 mg 1-chloro-4-(β-D-glucopyranos-1-yl)-2-[4-((S)-tetrahydrofuran-3-yloxy)-benzyl]-benzene (obtained as described above) are dissolved in 0.8 ml of ethyl acetate (containing 0.5-3% water) upon heating up to about 50° C. The solution is allowed to cool slowly (about 1 to 3 h) to about 20° C. After 48 h the crystalline form is isolated as white crystals by filtration. An excess of the solvent is removed by storing the crystals at elevated temperature (40 to 50° C) for about 3 to 4 h at reduced pressure.

Variant 2:

1 g 1-chloro-4-(β-D-glucopyranos-1-yl)-2-[4-((S)-tetrahydrofuran-3-yloxy)-benzyl]-benzene are dissolved in 5 ml of water/ethanol mixture (2:3 volume ratio) upon heating up to about 50° C. 8 ml of water are added and the solution is allowed to cool to about 20° C. in 1 to 3 h. After 16 h the crystalline form is isolated as white crystals by filtration. Excess solvent is removed by storing the crystals at elevated temperature (40 to 50° C.) for about 4 to 6 h.

Variant 3:

1 g 1-chloro-4-(β-D-glucopyranos-1-yl)-2-[4-((S)-tetrahydrofuran-3-yloxy)-benzyl]-benzene are dissolved in 11 ml of isopropanol upon heating up to about 50° C. The solution is allowed to cool to about 20° C. in 1 to 3 h. After 16 h the crystalline form is isolated as white crystals by filtration. Residual solvent is removed by storing the crystals at elevated temperature (40 to 50° C.) for about 4 to 6 h.

Variant 4:

8,9 g 1-chloro-4-(β-D-glucopyranos-1-yl)-2-[4-((S)-tetrahydrofuran-3-yloxy)-benzyl]-benzene are dissolved in 60 ml of water/ethanol mixture (2:3 volume ratio) upon heating up to about 50° C. The solution is allowed to cool to about 20° C. in 3 h and the crystalline compound is isolated by filtration. The separated white solid is dried at 40° C. for 16 h to yield about 6 g of the crystalline form.

The invention claimed is:

1. The crystalline form of 1-chloro-4-(β-D-glucopyranos-1-yl)-2-[4-(S)-tetrahydrofuran-3-yloxy)-benzyl]-benzene having an X-ray diffraction pattern that comprises peaks at 18.84, 20.36 and 25.21 degrees 2θ±0.05 degrees 2θ, wherein said X-ray powder diffraction is made using CuK$_{α1}$ radiation.

2. The crystalline form according to claim 1, wherein the X-ray powder diffraction pattern further comprises peaks at 14.69, 19.16 and 19.50 degrees 2 Θ±0.05 degrees 2 Θ, wherein said X-ray powder diffraction pattern is made using CuK$_{α1}$ radiation.

3. 1-Chloro-4-(β-D-glucopyranos-1-yl)-2-[4-((S)-tetrahydrofuran-3-yloxy)-benzyl]-benzene, wherein at least 50% of said 1-Chloro-4-(β-D-glucopyranos-1-yl)-2-[4-((S)-tetrahydrofuran-3-yloxy)-benzyl]benzene is present in the form of the crystalline form in accordance with claim 1.

4. A pharmaceutical composition comprising the crystalline form in accordance with claim 1.

5. A pharmaceutical composition comprising the crystalline form in accordance with claim 2.

6. A method for making the crystalline form in accordance with claim 1, said method comprising the following steps:
 (a) dissolving 1-chloro-4-(β-D-glucopyranos-1-yl)-2-]4-((S)-tetrahydrofuran-3-yloxy)-benzyl]-benzene in a solvent or a mixture of solvents to form a saturated or nearly saturated solution;
 (b) storing the solution to precipitate the crystalline form in accordance with claim 2 out of solution and thus to yield a suspension;
 (c) isolating the precipitate from the suspension; and
 (d) drying the precipitate until any excess of said solvent or mixture of solvents has been removed.

7. A method for making the crystalline form in accordance with claim 2, said method comprising the following steps:
 (a) dissolving 1-chloro-4-(β-D-glucopyranos-1-yl)-2-]4-((S)-tetrahydrofuran-3-yloxy)-benzyl]-benzene in a solvent or a mixture of solvents to form a saturated or nearly saturated solution;
 (b) storing the solution to precipitate the crystalline form in accordance with claim 3 out of solution and thus to yield a suspension;
 (c) isolating the precipitate from the suspension; and
 (d) drying the precipitate until any excess of said solvent or mixture of solvents has been removed.

* * * * *

UNITED STATES PATENT AND TRADEMARK OFFICE
CERTIFICATE OF CORRECTION

PATENT NO. : 7,713,938 B2  Page 1 of 1
APPLICATION NO. : 11/406971
DATED : May 11, 2010
INVENTOR(S) : Frank Himmelsbach et al.

It is certified that error appears in the above-identified patent and that said Letters Patent is hereby corrected as shown below:

In Column twelve (12), line six (6), in Claim 1, change "The" to --A--.

In Column twelve (12), line thirty-two (32), in Claim 6, change "2" to --1--.

In Column twelve (12), line forty-four (44), in Claim 7, change "3" to --2--.

Signed and Sealed this

Fifth Day of October, 2010

David J. Kappos
*Director of the United States Patent and Trademark Office*